(12) United States Patent
Trimble

(10) Patent No.: US 9,750,689 B2
(45) Date of Patent: Sep. 5, 2017

(54) TRANSDERMAL SILICONE GEL (SILOGEL) COMPOSITIONS AND METHODS OF PREPARATION

(71) Applicant: Humco Holding Group, Inc., Texarkana, TX (US)

(72) Inventor: John Olin Trimble, San Antonio, TX (US)

(73) Assignee: HUMCO HOLDING GROUP, INC., Texarkana, TX (US)

( * ) Notice: Subject to any disclaimer, the term of this patent is extended or adjusted under 35 U.S.C. 154(b) by 0 days.

(21) Appl. No.: 14/551,644

(22) Filed: Nov. 24, 2014

(65) Prior Publication Data

US 2015/0148355 A1     May 28, 2015

Related U.S. Application Data

(60) Provisional application No. 61/909,339, filed on Nov. 26, 2013.

(51) Int. Cl.

| | |
|---|---|
| *A61K 9/113* | (2006.01) |
| *A61K 47/36* | (2006.01) |
| *A61K 9/107* | (2006.01) |
| *A61K 31/522* | (2006.01) |
| *A61K 31/135* | (2006.01) |
| *A61K 31/192* | (2006.01) |
| *A61K 31/137* | (2006.01) |
| *A61K 31/196* | (2006.01) |
| *A61K 31/197* | (2006.01) |
| *A61K 31/445* | (2006.01) |
| *A61K 31/195* | (2006.01) |
| *A61K 47/34* | (2017.01) |
| *A61K 47/10* | (2017.01) |
| *A61K 47/24* | (2006.01) |
| *A61K 47/14* | (2017.01) |
| *A61K 9/00* | (2006.01) |
| *A61K 9/06* | (2006.01) |

(52) U.S. Cl.
CPC ............ *A61K 9/107* (2013.01); *A61K 9/0014* (2013.01); *A61K 9/06* (2013.01); *A61K 9/113* (2013.01); *A61K 31/135* (2013.01); *A61K 31/137* (2013.01); *A61K 31/192* (2013.01); *A61K 31/195* (2013.01); *A61K 31/196* (2013.01); *A61K 31/197* (2013.01); *A61K 31/445* (2013.01); *A61K 31/522* (2013.01); *A61K 47/10* (2013.01); *A61K 47/14* (2013.01); *A61K 47/24* (2013.01); *A61K 47/34* (2013.01); *A61K 47/36* (2013.01)

(58) Field of Classification Search
CPC ................................. A61K 47/36; A61K 9/113
See application file for complete search history.

(56) References Cited

U.S. PATENT DOCUMENTS

| | | | |
|---|---|---|---|
| 4,370,319 A | 1/1983 | Chapin et al. | |
| 4,960,764 A | 10/1990 | Figueroa, Jr. et al. | |
| 6,461,600 B1 | 10/2002 | Ford | |
| 6,638,981 B2 | 10/2003 | Williams et al. | |
| 2007/0207107 A1 | 9/2007 | Winckle et al. | |
| 2009/0232856 A1* | 9/2009 | Patel | A61K 8/066 424/401 |
| 2009/0285869 A1* | 11/2009 | Trimble | A61K 8/042 424/401 |
| 2010/0008958 A1 | 1/2010 | Mundschau et al. | |
| 2013/0165420 A1 | 6/2013 | Ray, II et al. | |

FOREIGN PATENT DOCUMENTS

| | | |
|---|---|---|
| AU | 2012-202-807 A1 | 5/2012 |
| AU | 2012202807 | 5/2012 |
| WO | 01/91703 | 12/2001 |
| WO | 01-91703 A2 | 12/2001 |
| WO | 2008/134712 | 11/2008 |
| WO | 2008-134712 A2 | 11/2008 |

OTHER PUBLICATIONS

European Patent Office; PCT Application No. PCT/US2014/067090; Second Written Opinion; Nov. 9, 2015.
European Patent Office; PCT Application No. PCT/US2014/067090; Response to Second Written Opinion; Jan. 4, 2016.
The International Preliminary Report on Patentability issued by European Patent Office; PCT Application No. PCT/US2014/067090 on Feb. 8, 2016.
Jorge et al., "Topical preparations for pain relief: efficacy and patient adherence", Journal of Pain Research, 2011, vol. 4, pp. 11-24.

* cited by examiner

*Primary Examiner* — Robert Havlin
(74) *Attorney, Agent, or Firm* — Jackson Walker LLP

(57) ABSTRACT

A silicone gel ("silogel") composition used to deliver pharmaceutical products transdermally as well as a method for producing the silogel composition, which may contain up to 80% additive ingredients. Preferred embodiments of the invention may include silogel compositions which provide high viscosity/no separation due to API. They are not temperature-sensitive, have no shear stress from the ointment mill/EMP, have no gumming up/stickiness, and no hardening.

1 Claim, 2 Drawing Sheets

TRANSDERMAL SILICONE GEL (SILOGEL) COMPOSITIONS AND METHODS OF PREPARATION

RELATED APPLICATIONS

This application claims priority to U.S. Provisional Patent Application Ser. No. 61/909,339, entitled "TRANSDERMAL SILICONE GEL (SILOGEL) COMPOSITIONS AND METHODS OF PREPARATION," filed Nov. 26, 2013, the entire content of which is incorporated by reference.

BACKGROUND

The present invention relates to transdermal silicone gel ("silogel") compositions and methods for pain management. The invention provides water-in-silicone emulsions comprising a nonsteroidal anti-inflammatory drug; an opioid drug; an adjuvant drug acting on voltage-gated channels; an adjuvant drug acting on gamma-aminobutyric acid receptors; an adjuvant drug acting on acute musculoskeletal pain; an adjuvant drug acting as an antidepressant; a silicone component; water; and a surfactant.

Silicone Emulsions

Silicone emulsions need to have both water soluble and oil soluble portions. The traditional oil soluble portion is fatty. Silicone surfactants substitute or add on silicone based hydrophobicity. This results in emulsions that have the substantivity, lower irritation, skin feel and other attributes of silicone in addition to the properties one expects from the fatty surfactant. In emulsions where silicone is predominant, the functional attributes of silicone will predominate. If the emulsion has both a silicone and fatty hydrophobe present, it will function with attributes of both of the materials. This allows for the formulation of a wide variety of emulsions that have oil, water, silicone, and variable solubility.

Silicone surfactants can be polymeric or oligomeric and can possess one or more hydrophilic functional groups. Moreover the nature of functional groups can be ionic or non-ionic. In contrast to low-molecular-weight surfactants, multifunctional polymeric emulsifiers can attach to an interface via several segments. The energy of adsorption is equal to the sum of the interactions of all segments, and can be considerably greater than the energy of individual monomeric surfactants. Hence these multifunctional polymeric emulsifiers can adsorb very strongly at an interface. They can be used in low dosages and are very efficient in generating highly stable emulsions. Polymers neither readily desorb from an interface, nor migrate through the bulk phase because of their strong adsorption at the interface.

Analgesic therapies for acute and chronic pain conditions currently rely on three major classes of drugs: nonsteroidal anti-inflammatory drugs, opioids, and a group of drugs with diverse pharmacological actions collectively known as adjuvants. By definition, topical drugs used to control pain will act locally on damaged or dysfunctional soft tissues or peripheral nerves. Their actions may be on the inflammatory response itself or on sensory neurons.

Nonsteroidal anti-inflammatory drugs are among the most widely used of all therapeutic classes of drugs. These agents have been understood for many years to act peripherally to reduce the production of prostaglandins that sensitize nerve endings at the site of injury. This effect occurs due to inhibition of the cyclooxygenase enzyme that converts arachidonic acid liberated from the phospholipid membrane by phospholipases to prostanoids such as prostaglandins. Examples of nonsteroidal anti-inflammatory drugs include, but are not limited to, acetylsalicylic acid, diclofenac, flurbiprofen, ibuprofen, indomethacin, ketoprofen, ketorolac, meloxicam, naproxen, and piroxicam.

Opioid drugs act on receptors present on the peripheral terminals of thinly myelinated and unmyelinated cutaneous sensory fibers. Dorsal root ganglia contain mRNA for opioid receptors, and when synthesized, these receptors are transported peripherally. Peripheral opioid actions are not prominent in normal tissue but appear early after the induction of inflammation. Although inflammation enhances opioid receptor expression and transport to peripheral, this process takes days and the initial expression of analgesia precedes these changes. Examples of opioid drugs include, but are not limited to, fentanyl, loperamide, methadone, morphine, oxycodone, and tramadol.

Adjuvant drugs acting on voltage-gated channels play a fundamental role in the control of neuronal excitability. Alterations in the expression, distribution, and function of voltage-gated channels that occur following nerve injury or chronic inflammation have a profound effect on the firing of primary afferent neurons and contribute to the expression of pain behaviors. Examples of adjuvant drugs acting on voltage-gated channels include, but are not limited to, benzocaine, bupivacaine, dibucaine, diphenhydramine, etidocaine, gabapentin, lidocaine, mepivacaine, nifedipine, pregabalin, prilocalne, procaine, ropivacaine, tetracaine, and verapamil.

Adjuvant drugs acting on gamma-aminobutyric acid ("GABA") receptors can modulate peripheral pain signaling. Endogenous peripheral GABA could arise from primary afferent fibers that contain glutamate, and GABA receptors are present on some unmyelinated afferent axons. Examples of adjuvant drugs acting on gamma-aminobutyric acid receptors include, but are not limited to, baclofen, clonazepam, lorazepam, and tiagabine.

Adjuvant drugs acting on acute musculoskeletal pain are a misnomer, because most medications in this class have little or no direct action on the contractile mechanisms of striated skeletal muscle. Because many of these medications were initially used as treatment for nonspecific back pain typically labeled as a strain, sprain, or mechanical back pain, these drugs were considered muscle relaxants. It is unclear whether these medications actually decrease painful muscle spasm or if they exert other effects. Examples of adjuvant drugs acting on acute musculoskeletal pain include, but are not limited to, acyclovir, capsaicin, captopril, carisoprodol, chlorzoxazone, clonidine, cyclobenzaprine, deoxy-d-glucose, dexamethasone, dexmedatomidine, guaifenesin, orphenadrine, metaxalone, methocarbamol, methylsulfonylmethane, pentoxifylline, and tizanidine.

Adjuvant drugs acting on N-methyl-D-aspartate ("NMDA") receptors are proposed for the treatment of neuropathic pain. Evidence suggests that NMDA receptors within the dorsal horn play an important role in both inflammation and nerve injury-induced central sensitization. Examples of adjuvant drugs acting on NMDA receptors include, but are not limited to, amantadine, carbamazepine, dextromethorphan, ketamine, memantine, and phenyloin.

Adjuvant drugs acting as an antidepressant can treat pain by adjusting levels of neurotransmitters. These medicines can increase the availability of the body's signals for well-being and relaxation, enabling pain control for people with chronic pain conditions that do not completely respond to the usual treatments. Examples of adjuvant drugs acting as an antidepressant include, but are not limited to, amitriptyline, bupropion, citalopram, dehydroepiandrosterone, desipramine, desvenlafaxine, doxepin, duloxetine, fluoxetine, imipramine, minalcipran, nortriptyline, paroxetine, promethazine, sertraline, and venlafaxine.

Several different compositions for topical compositions have been described.

U.S. Pat. No. 4,370,319 to Chapin, et al., issued Jan. 25, 1983, discloses skin conditioning compositions comprising an alkali metal phosphoric acid ester salt of a partial glyceride, silicone fluid, a long chain alkyl ester of a fatty acid, an emollient material, an emulsifier and water. The phosphated glyceride and the dimethicone fluid serve to provide greater retention of the conditioning composition on the skin.

U.S. Pat. No. 4,960,764 to Figueroa, et al., issued Oct. 2, 1990, teaches an oil-in-water-in-silicone fluid emulsion composition comprising a silicone fluid continuous phase, an aqueous discontinuous phase comprising an oil-in-water emulsion, and an effective dispersing amount of dimethicone copolyol. It has now been found that a skin moisturizing multiphase emulsion composition may be provided wherein the continuous phase consists essentially of a silicone fluid component and, in addition, an effective dispersing amount of a particular silicone fluid, namely, dimethicone copolyol, is used to disperse in said continuous phase an oil-in-water emulsion as the aqueous discontinuous phase, the oil phase of said o/w emulsion being a liquid non-particulate containing material.

U.S. Pat. No. 6,461,600 to Ford, et al., issued Oct. 8, 2002, discloses a cream-type carrier for topical delivery of medicaments including analgesics. The carrier comprises a mixture of: squalane NF, an emulsifier such as Tween 80, glycerin, cetyl alcohol NF, glyceryl monostearate, lecithin organogel preserved, BHT, urea USP, EDTA, water, stearic acid, simethicone USP, and ethoxy diglycol reagent. The invention also comprises a combination of the carrier, with either or both of ketamine hydrochloride and amitriptyline hydrochloride, which has use as a topically applied analgesic.

U.S. Pat. No. 6,638,981 to Williams, et al., issued Oct. 28, 2003, teaches topical compositions and methods for treating pain. The invention provides oil-in-water emulsions comprising an antidepressant; an NMDA receptor antagonist; a lipophilic component; water; and a surfactant. The compositions induce a local-anesthetic effect when topically administered to intact skin thereby treating or preventing pain, for example, neuropathic pain.

Professional Compounding Centers of America ("PCCA") manufactures Anhydrous Lipoderm. It is designed for Active Pharmaceutical Ingredients ("APIs") that are unstable in water. It has good salt resiliency. Select formulations have low viscosity/separation, and are temperature-sensitive.

PCCA also manufactures Lipoderm HMW. It is designed to deliver drugs with high molecular weights through the skin. It is stable from pH 4-pH 6, but has low salt resiliency. Select formulations have low viscosity/separation.

PCCA further manufactures Lipoderm Original. It is designed to deliver APIs through the skin. It is stable from pH 3-pH 9, and has good salt resiliency. Select formulations have low viscosity/separation due to API, shear stress from the ointment mill/EMP, and gumming up/stickiness.

PCCA also manufactures Lipoderm ActiveMax. It is designed to hold more single-ingredient salt forms without losing the skin permeation efficacy. It is stable from pH 3-pH 9, and has better salt resiliency. Select formulations have low viscosity/separation, hardening, and gumming up/stickiness.

Almost all of the above topical compositions achieve some tissue-levels of active compounds, reducing blood-level related side effects. Many of the commercial topical compositions have low viscosity/separation due to API, shear stress from the ointment mill/EMP, gumming up/stickiness, hardening, and are temperature-sensitive. They do not satisfy the demand of varying active compounds, as well as pharmacists' demands for time-efficient and uniform compounding, and patients' demands for cosmetic and efficacious prescriptions. The present invention overcomes many of these problems.

Ternary Systems

Ternary emulsions, often termed double emulsions, are complex liquid dispersion systems known also as emulsion-of-emulsion, where the liquid dispersion droplets are further dispersed in another liquid. The inner dispersed droplets in the double emulsions are separated from the outer liquid phase by a layer of another phase. Usually the size of the droplets of the inner emulsion is small while the size of the outer emulsion globules can be significantly larger. These types of emulsions are particularly important when protection of the internal phase is required. The structure of silicone vesicles opens a wide range of possibilities for the incorporation of useful active ingredients. For example, using silicone vesicles, hydrophilic and hydrophobic actives can be separated and protected from each other. This protection is obtained because the hydrophobic actives can be distributed inside the bilayer, while hydrophilic actives will necessarily be in solution in the water phase. It has been demonstrated that permeability of the bilayer to water-soluble actives can be very low, and this phenomenon prevents the active from escaping from the silicone vesicle.

Polymeric surfactants are typically chosen to stabilize such emulsion systems because they adsorb at the interface more strongly than monomeric surfactants. Macromolecular surfactants have the advantage of attaching to a surface via several segments. Even if the free energy of adsorption per segment is low, the attachment of several segments leads to a large total free energy of adsorption. As a result, their adsorption onto surfaces is less reversible and they can be used efficiently even at lower concentrations. Polymers can stabilize the droplets via both steric and depletion stabilization mechanisms. Polysiloxanes grafted with non-ionic polyethylene oxide moieties have proven to be excellent steric stabilizers for this kind of emulsion. The high emulsifying power of silicone-derived polymers, their strong adsorption to the Water-in-Oil ("W/O") interface and the pronounced elasticity of the interfacial film, are the basis for the stability of double emulsions with silicones. Few commercial applications of double emulsions are known and this can be attributed to their thermodynamic instability and the uncontrolled, fast release of entrapped materials such as electrolytes or other dispersed materials. These emulsions are potential systems for sustained and slow release with possible applications in the areas of pharmaceuticals. Such emulsions can also develop high viscosity, which is desired in pharmaceutical applications for creams and lotions.

Preparation of Silogel

Silogel may be prepared by mixing an oil phase with inorganic hydrocolloid, organic hydrocolloid and silicone emulsifier phases using a high-shear mixing method. Oil Phase: charge kettle with Light Mineral Oil and Procol CS-20-D; install mixer; heat to 75°-80° C.; turn on the mixer. Inorganic Hydrocolloid Phase: in tank equipped with mixer, add Purified Water; turn on the mixer; heat to 75-80° C.; add Veegum HS and mix until dissolved. Organic Hydrocolloid Phase: in tank equipped with mixer, add Poloxamer 407 30% Solution and Simulgel NS: turn on the mixer; cool to 5°-10° C.; add Structure XL and mix until dissolved. Silicone Emulsifier Phase: in tank equipped with mixer, add Dow Corning 556; turn on the mixer; heat to 75°-80° C.; add Dow Corning AMS-C30 and mix until dissolved. Emulsion Phase: combine the Oil Phase, the Inorganic Hydrocolloid Phase, the Organic Hydrocolloid Phase, and the Silicone Emulsifier Phase in kettle with mixing; with mixing, add Lecithin 50% Solution, Germaben II-E, Euxyl PE9010, Aloe Vera Oil, Dow Corning 200-350, and Vitamin E Oil; mix for 1 hour; transfer to a storage vat.

Silogel is composed of emulsifiers, hydrocolloids, and lecithin. It is a third generation pluronic lecithin organogel ("PLO"). The advantages of the silogel compared to the previous PLOs are that it has excellent spreading and film-forming properties, gloss, and a dry non-sticky feel; it has good flow properties even at low temperatures, good thermal and oxidative resistance, low surface tension, and can use larger amounts of hydrophilic or lipophilic active substances without lessening storage stability; it has sustained and controlled release of a wide range of pharmaceutical actives.

Dispersion of a hydrophilic drug in the aqueous phase is conducted by dissolving the drug with hydrophilic silicone copyols, along with alkyl-modified polyacrylates and monomeric surfactants, to make Silicone-in-Water-in-Oil ("S/W/O") emulsions. Hydrophilic drugs have an uptake capacity of about 30% to about 35%.

Dispersion of a lipophilic drug in the oil phase is conducted by dissolving the drug with silicone copyols with various alkyl chains compatible with hydrocarbon oils, to make W/O emulsions. Lipophilic drugs have an uptake capacity of about 30% to about 35%.

Characteristics of Silogel

Silogel must have the ability to absorb or rub in quickly, have no residue or pore clogging effect, have a non-sticky feel, and have no skin shine. Products such as baby oil that have alight, oily feel on the skin have been generally accepted by consumers; those that feel greasy, such as petroleum jelly, have not. However, oiliness and greasiness are only two of twelve parameters that can be used to compare the sensory characteristics of products. Using guidelines recommended by ASTM Committee E18.03.01 on Sensory Evaluation, one can construct a sensory profile to scientifically evaluate feel. Sensory profiles of various grades of mineral oil and silicone provide useful comparisons of the materials. (DiSapio, A., The Evolving Role of Silicones: Versatile Alternatives to Hydrocarbons, from "Soap Cosmetics Chemical Specialties," 1994).

Silogel must aid in the formulation of stable, aesthetically pleasing pharmaceutical emulsions with high water levels, while requiring no heat during processing. Silicone polymers comprising a non-ionic hydrophilic group and a hydrophobic polydimethyl siloxane chain have emulsifying properties. The molecular architecture of these polymers can be tailored to suit specific applications. In most cases, the hydrophilic moiety of choice has been polyoxyethylene ("EO") because of its good water solubility and ease of synthesis with a wide range of molecular weights. The hydrophilicity/hydrophobicity of these polymers can be controlled by varying the chain length of EO groups, partial or complete substitution of EO with polyoxypropylene ("PO"), or by varying the degree of modification in the case of grafted polymers. Silicone copyols can also be modified with various alkyl chains in order to make them compatible with hydrocarbon oils, thereby making them good stabilizers for emulsions of hydrocarbon oil and water. (Somasundaran, P., Silicone Emulsions, from "Advances in Colloid and Interface Science," 2006).

Silogel must entrap, deliver and subsequently release water- or oil-soluble substances. Encapsulation of actives within the silicone vesicles is possible for compositions containing 0.1 to 40% silicone polyether and 0.1 to 10% of the active substance. Homogenization techniques reduce and narrow the size of silicone vesicles. (Newton, J., Silicone Technologies as Delivery Systems via Physical Association, from "Cosmetics and Toiletries," 2004).

Silogel in the Delivery of Pain Management Drugs

A wide range of Anhydrous Ointment is commercially available. Maximum pain management anhydrous ointments include Benzocaine 5% Ointment, Capsaicin 1.5% Ointment, and Carbamazepine 3% Ointment. Select formulations have low viscosity/separation due to API, and are temperature-sensitive.

A wide range of Pluronic Lecithin Organogel ("PLO") is commercially available. In addition to anhydrous ointment drugs, maximum pain management PLOs include Aceclofenac 1.5% PLO, Acyclovir 5% PLO, Amitriptyline 10% PLO, Baclofen 5% PLO, Captopril 0.1% PLO, Clonidine 0.22% PLO, Cyclobenzaprine 2% PLO, Dehydroepiandrosterone 2.5% PLO, Deoxy-D-Glucose 2% PLO, Dexamethasone 2% PLO, Dextromethorphan 20% PLO, Diclofenac 3% PLO, Fentanyl 0.01% PLO, Fluoxetine 5% PLO, Gabapentin 6% PLO, Ibuprofen 10% PLO, Indomethacin 2% PLO, Ketamine 11.5% PLO, Ketoprofen 10% PLO, Lidocaine 10% PLO, Lorazepam 0.1% PLO, Meloxicam 1.5% PLO, Methadone 2% PLO, Morphine 5% PLO, Naproxen 20% PLO, Nifedipine 2% PLO, Oxycodone 1% PLO, Piroxicam 2% PLO, Promethazine 1.25% PLO, Tetracaine 5% PLO, and Tramadol 5% PLO. Select formulations have low viscosity/separation due to API.

A wide range of Oil-in-Water Lecithin Organogel ("O/W LO") is now commercially available. In addition to anhydrous ointment and PLO drugs, maximum pain management O/W LOs include Bupivacaine 1% O/W LO, Ketoprofen 20% O/W LO, Methylsulfonylmethane 10% O/W LO, and Pentoxifylline 5% O/W LO. Select formulations have low viscosity/separation due to API, shear stress from the ointment mill/EMP, and gumming up/stickiness.

A wide range of Water-in-Oil Lecithin Organogel ("W/O LO") is now commercially available. In addition to anhydrous ointment, PLO, and W/O LO drugs, maximum pain management W/O LOs include Gabapentin 10% W/O LO. Select formulations have low viscosity/separation due to API, hardening, and gumming up/stickiness.

SUMMARY

The present invention relates to a transdermal pharmaceutical delivery composition, utilizing matrices of a silogel. In particular, this invention relates to compositions which may comprise an oil phase containing optional hydrophilic and lipophilic silicone copyols, organic oil-in-water ("O/W") and W/O emulsifiers, and an internal aqueous phase comprising inorganic and organic hydrocolloids. These silicone copyols are based on the ability of these materials to function differently from organic emulsifiers. They migrate to the interface between the two phases, stay at that interface, and stabilize the repulsion forces of the two phases.

The current invention comprises a silogel composition which could be used to deliver pharmaceutical products transdermally. The invention further comprises a method for producing the silogel composition, which may contain a maximum combination of 35% ionic and non-ionic active drugs, and a maximum internal phase of 80% water. Increasing this internal water phase increases viscosity, and increasing emulsifiers and hydrocolloids reduces particle size to avoid settling.

Preferred embodiments of the invention may include silogel compositions which have high viscosity/no separation due to API, are not temperature-sensitive, have no shear stress from the ointment mill/EMP, have no gumming up/stickiness, and no hardening. These rheological improvements are dependent on increased water phase volume, oil polarity, and water phase electrolyte.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF PREFERRED EMBODIMENTS

Figure 1:
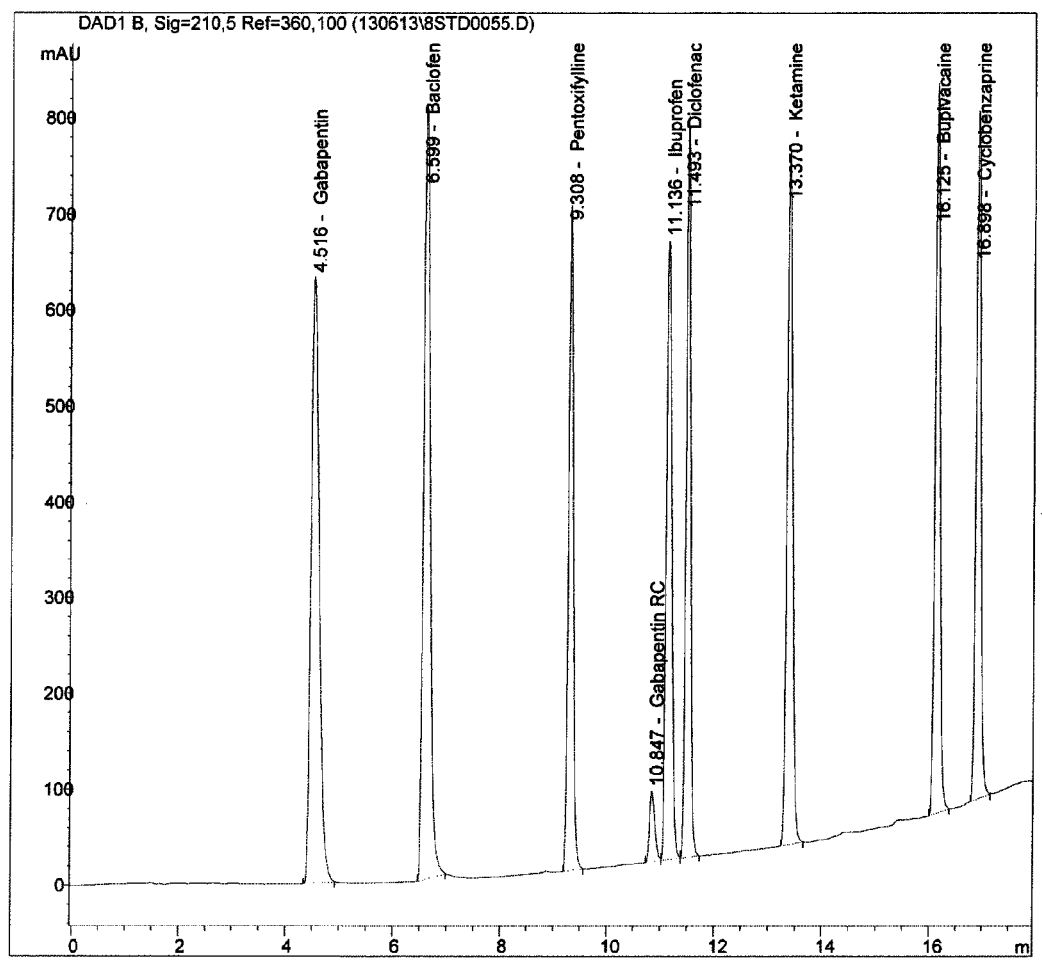
FIG. 1 shows the HPLC chromatogram of Gabapentin (6%)/Baclofen (2%)/Pentoxifylline (3%)/Ibuprofen (3%)/Diclofenac (5%)/Ketamine (10%)/Bupivacaine (1%)/Cyclobenzaprine (2%).
Figure 2:
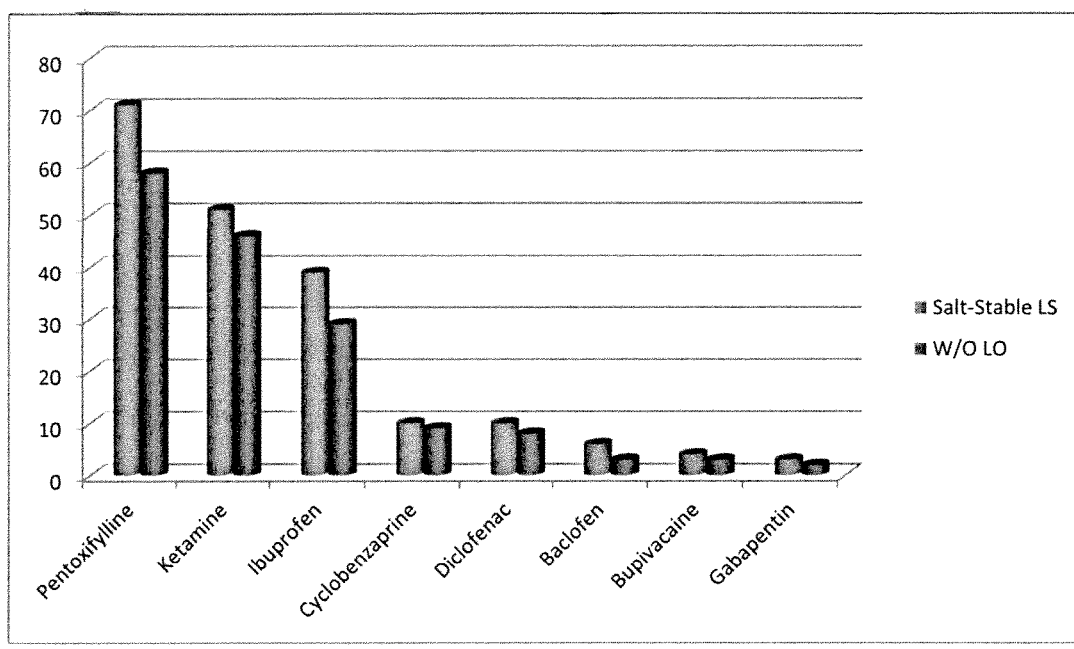
FIG. 2 shows the total percent of applied dose that penetrated past the Stratum Corneum with a preferred embodiment of the invention ("Salt-Stable LS Advanced") and a standard water-in-oil lecithin organogel ("Standard W/O LO").

One aspect of the current invention pertains to a silogel composition which may be used to deliver pharmaceutical products transdermally. The invention further comprises a method for producing the silogel composition, which may contain up to 80% additive ingredients. Preferred embodiments of the invention may include silogel compositions which provide high viscosity/no separation due to API, are not temperature-sensitive, have no shear stress from the ointment mill/EMP, have no gumming up/stickiness, and no hardening.

Composition

A preferred embodiment of the silogel composition comprises hydrophilic silicone copolyols with varying chain length of EO groups, preferably in the range of about 10 to about 19 groups, partial or complete substitution of EO with PO, or varying degree of modification of grafted polymers. Examples may include PEG/PPG-18/18 dimethicone, PEG-12 dimethicone, PEG/PPG-19/19 dimethicone, PEG-10 dimethicone, and PEG/PPG-16/16 dimethicone. The hydrophilic silicone copolyol may be present in a concentration range of 0.1% to 4.0%, preferably 1.0% to 3.0%, most preferably 1.5% to 2.5%.

This embodiment of the invention further comprises lipophilic silicone copolyols with various alkyl chain length, preferably about 12 to about 18 alkyl groups, compatible with hydrocarbon oils. Examples may include lauryl PEG/PPG-18/18 dimethicone, isobutyl PEG/PPG-10/7 dimethicone, and C30-45 dimethicone. The lipophilic silicone copolyol may be present in a concentration range of 0.1% to 4.0%, preferably 1.0% to 3.0%, most preferably 1.5% to 2.5%.

This embodiment of the invention further comprises organic O/W emulsifier agents with a hydrophile-lipophile balance ("HLB") value from about 8 to about 18. Examples may include ceteth-15, ceteth-16, ceteth-20, ceteareth-6, ceteareth-12, ceteareth-15, ceteareth-16, ceteareth-20, ceteareth-25, isoceteth-20, steareth-10, steareth-20, oleth-5, oleth-10, oleth-15, oleth-20, laureth-15. PEG-20 stearate. PEG-25 stearate, PEG-20 oleate, PEG-20 sorbitan stearate, PEG-20 sorbitan oleate, sodium laureth-11 carboxylate, sodium lauryl ether sulfate, PEG-30 cholesteryl ether, PEG-60 evening primrose glyceride. PEG-45 palm kernel glyceride, PEG-20 glyceryl laurate, and PEG-20 glyceryl stearate. The organic O/W emulsifier agent may be present in a concentration range of 1.0% to 20.0%, preferably 5.0% to 15.0%, most preferably 7.5% to 12.5%.

This embodiment of the invention further comprises organic W/O emulsifier agents with a HLB value from about 1 to about 8. Examples may include glyceryl caprinate, glyceryl caprylate, glyceryl dilaurate, glyceryl laurate, glyceryl linoleate, glyceryl oleate, glyceryl ricinoleate, glyceryl stearate, glycerol isostearate, diglycerol isostearate, triglycerol diisostearate, sorbitan isostearate, propylene glycol isostearate, propylene glycol stearate, polyglyceryl-3 methylglucose distearate, methylglucose sesquistearate, and polyglyceryl-2 dipolyhydroxystearate. The organic W/O emulsifying agent may be present in a concentration range of 1.0% to 20.0%, preferably 5.0% to 15.0%, most preferably 7.5% to 12.5%.

This embodiment of the invention further comprises an inorganic hydrocolloid with modified or unmodified, naturally occurring or synthetic sheet silicates. Examples may include bentonites such as magnesium aluminum silicate, quaternium-18 bentonite and stearalkonium bentonite, hectorites such as sodium magnesium silicate, quaternium-18 hectorite and stearalkonium hectorite, and hydrotalcites such as magnesium aluminum silicate synthesized with long-chain, organic and ammonium salts. The inorganic hydrocolloid may be present in a concentration range of 0.1% to 4.0%, preferably 1.0% to 3.0%, most preferably 1.5% to 2.5%.

This embodiment further comprises an organic hydrocolloid with long-chain, straight or branched polysaccharides that contain hydroxyl groups that can bond to water molecules. The organic hydrocolloid may be about 250 to about 2500 units in length. Examples may include gums such as gum arabic, gum karaya, gum tragacanth, gum ghatti, agar-agar, guar gum, locust bean gum, konjac, alginates, carrageenans, pectin, tara gum, xanthan gum, gellan gum, pullulan, curdlan, cellulose, microcrystalline cellulose, carboxymethylcellulose gum, methylcellulose, hydroxypropylcellulose, gelatin and chitosan, polymers such as acrylates/alkyl acrylate copolymer, acrylates/alkyl acrylate crosspolymer, acryloyldimethyltaurate copolymer and acryloyldimethyltaurate crosspolymer, and starches such as hydroxypropyl starch phosphate. The organic hydrocolloid may be present in a concentration range of 0.1% to 4.0%, preferably 1.0% to 3.0%, most preferably 1.5% to 2.5%.

This embodiment further comprises a biocompatible surfactant with phosphatidylcholine. Biocompatible surfactants include naturally occurring unsaturated lecithins. Examples may include soy bean lecithin and egg yolk lecithin. The biocompatible surfactant may be present in a concentration range of 0.1% to 5.0%, preferably 1.0% to 4.0%, most preferably 2.0% to 3.0%.

This embodiment further comprises a nonpolar solvent with an ability to form gel in the presence of lecithin. Nonpolar solvents include alkanes, esters and amines. Examples may include alkanes such as cyclopentane, cyclooctane, trans-decalin, trans-pinane, n-pentane, n-hexane, n-hexadecane and mineral oil, esters such as ethyl laureate, ethyl myristate, isopropyl myristate and isopropyl palmitate, and amines such as tripropylamine. The nonpolar solvent may be present in a concentration range of 1.0% to 50.0%, preferably 10.0% to 40.0%, most preferably 20.0% to 30.0%.

If desired, a saturated fatty alcohol such as myristyl alcohol, pentadecanol, cetyl alcohol, cetearyl alcohol, stearyl alcohol, nonadecanol, arachidyl alcohol, heneicosanol, behenyl alcohol, brassidyl alcohol, lignoceryl alcohol, ceryl alcohol and myricyl alcohol may be used in the present invention. The fatty alcohol has the ability to provide a transitory effect on membrane permeability. The saturated fatty alcohol may be present in a concentration range of 0.1% to 5.0%, preferably 1.0% to 4.0%, most preferably 2.0% to 3.0%.

If desired, a moisturizer such as aloe vera oil, dimethicone, glycerin, phenyl trimethicone, vitamin E oil, and wheat germ oil may be used in the present invention. The moisturizer stabilizes the skin prior to transmigration of the active agent and assists the skin to repair any damage. The moisturizer may be present in a concentration of 0.1% to 5.0%, preferably 1.0% to 4.0%, most preferably 2.0% to 3.0%.

If desired, an antimicrobial agent such as diazolidinyl urea, ethylhexylglycerin, methylparaben, phenoxyethanol, and propylparaben may be included in the present invention. The antimicrobial agent is equally effective against bacteria, yeasts and mould fungi. The antimicrobial agent may be present in a concentration of 1.0% to 2.0%, preferably 1.2% to 1.8%, most preferably 1.4% to 1.6%.

Methods

The silogel composition may be prepared be blending the proper amounts and ratios of all the required ingredients together.

One embodiment of the invention would include preparation as follows:

OIL PHASE: Charge a stainless steel tank with Light Mineral Oil. Add Procol CS-20-D. Heat to 75-80° C.; mix for 30 minutes or until homogenous.

INORGANIC HYDROCOLLOID PHASE: Charge a stainless steel tank with Purified Water. Heat to 35-40° C.; add Veegum HS; mix for 2 hours or until homogenous.

ORGANIC HYDROCOLLOID PHASE: Charge a double-motion kettle with Purified Water; heat to 35-40° C. Turn on the mixer/sweeper to 60 Hz. Add Poloxamer 407 30% Solution. Add Simulgel NS. Add Structure XL. Increase the mixer/sweeper to 90 Hz. Mix and sweep for 2 hours or until homogenous.

SILICONE EMULSIFIER PHASE: Charge a stainless steel tank with Dow Corning 556. Add Dow Corning AMS-C30. Heat to 75-80° C.; mix for 30 minutes or until homogenous.

EMULSION PHASE: Turn on the triple-motion kettle mixer/sweeper/emulsifier to 60 Hz. Add INORGANIC HYDROCOLLOID PHASE to ORGANIC HYDROCOLLOID PHASE. Increase the mixer/sweeper/emulsifier to 90 Hz. Mix, sweep and emulsify for 30 minutes or until homogenous. Decrease the mixer/sweeper/emulsifier to 60 Hz. Heat to 75-80° C. Add OIL PHASE. Add SILICONE EMULSIFIER PHASE. Maintain temperature at 75-80° C. Increase the mixer/sweeper/emulsifier to 90 Hz. Mix, sweep and emulsify for 20 minutes or until homogenous. Decrease the mixer/sweeper/emulsifier to 60 Hz. Cool to 35-40° C. Add Lecithin 50% Solution. Mix, sweep and emulsify for 20 minutes or until homogenous. Decrease the mixer/sweeper/emulsifier to 30 Hz. Cool to 25-30° C. Add Germaben II-E. Add Euxyl PE9010. Add Aloe Vera Oil. Add Dow Corning 200-350. Add Vitamin E Oil. Mix, sweep and emulsify for 20 minutes or until homogenous.

EXAMPLE

| Ingredient | Description | Amount |
| --- | --- | --- |
| Purified Water | Purified Water | 55.68 w/w |
| VEEGUM HS (Vanderbilt Minerals LLC, Norwalk CT) | Magnesium aluminum silicate, purified smectite clay, an inorganic hydrocolloid | 1.50 w/w |
| POLOXAMER 407 (Sigma Aldrich, St. Louis, MO) | Organic O/W emulsifier | 3.00 w/w |
| SIMULGEL NS (Seppic, Puteaux Cedex, France) | Hydroxyethyl acrylate, sodium acryloyldimethyl taurate copolymer, squalane, polysorbate 60, organic hydrocolloids, an organic W/O emulsifier | 1.90 w/w |
| STRUCTURE XL (AkzoNobel, Amsterdam) | Hydroxypropyl starch phosphate, an organic hydrocolloid | 0.10 w/w |
| Light Mineral Oil | Non-polar solvent | 18.00 w/w |
| PROCOL CS-20-D (Protameen Chemicals Inc., Totowa, NJ) | Cetearyl alcohol, ceteareth-20, a saturated fatty alcohol, an organic O/W emulsifier | 10.00 w/w |
| Dow Corning AMS-C30 (Dow Corning, Midland, MI) | C30-45 dimethicone, a lipophilic silicone copolyol | 2.50 w/w |
| Dow Corning 556 | Phenyl trimethicone, a moisturizer | 2.00 w/w |
| Lecithin | Biocompatible surfactant | 0.33 w/w |
| Isopropyl Palmitate | Non-polar solvent | 0.33 w/w |
| Aloe Vera Oil | Moisturizer | 1.00 w/w |
| Dow Corning 200-350 | Dimethicone, a moisturizer | 1.00 w/w |
| EUXYL PE9010 (Schulke & Mayr, Norderstedt, Germany) | Phenoxyethanol, ethylhexylglycerin, an antimicrobial agent | 1.00 w/w |
| GERMABEN II-E (Ashland, Inc., Covington, KY) | Propylene glycol, diazolidinyl urea, methylparaben, propylparaben, an antimicrobial agent | 1.00 w/w |
| Vitamin E Oil | Moisturizer | 0.66 w/w |

Simultaneous hydrophilic and lipophilic drug uptake capacity experiments were conducted by dissolving 2.0% Baclofen, 1.0% Bupivacaine, 2.0% Cyclobenzaprine, 5.0% Diclofenac, 6.0% Gabapentin, 3.0% Ibuprofen, 10.0% Ketamine and 3.0% Pentoxifylline into the current invention ("Salt-Stable LS Advanced"). Singular drugs are reported to have an uptake capacity of only 10% in Standard PLO. See Jorge, L., et al., Journal of Pain Research, Topical Preparations for Pain Relief—Efficacy and Patient Adherence, Vol. 4, No. 11-24, 2011. The Salt-Stable LS Advanced sample shows a steady simultaneous permeation of up to 71%. The percent of applied dose that penetrated past the stratum corneum with Salt-Stable LS Advanced was up to 7.1 times more than Standard PLO.

| Percutaneous Absorption Testing | 2 Hours | 4 Hours | 8 Hours | 12 Hours | 24 Hours | 32 Hours | 48 Hours |
|---|---|---|---|---|---|---|---|
| Pentoxifylline | 3% | 7% | 26% | 34% | 53% | 71% | 71% |
| Ketamine | 4% | 7% | 20% | 25% | 38% | 51% | 51% |
| Ibuprofen | 5% | 8% | 19% | 20% | 30% | 39% | 39% |
| Cyclobenzaprine | 0% | 2% | 3% | 5% | 7% | 8% | 10% |
| Diclofenac | 0% | 1% | 4% | 4% | 7% | 10% | 10% |
| Baclofen | 0% | 1% | 2% | 3% | 4% | 5% | 6% |
| Bupivacaine | 0% | 1% | 1% | 2% | 3% | 4% | 4% |
| Gabapentin | 0% | 0% | 1% | 2% | 2% | 3% | 3% |

REFERENCES CITED

The following references, to the extent that they provide exemplary procedural or other details supplementary to those set forth herein, are specifically incorporated herein by reference.

U.S. PATENT DOCUMENTS

U.S. Pat. No. 4,370,319 to Chapin, et al., issued Jan. 25, 1983
U.S. Pat. No. 4,960,764 to Figueroa, Jr., et al., issued Oct. 2, 1990
U.S. Pat. No. 6,461,600 to Ford, et al., issued Oct. 8, 2002
U.S. Pat. No. 6,638,981 to Williams, et al., issued Oct. 28, 2003

REFERENCES

O'Lenick, A., et al., Silicone Spectator, Silicone Emulsions and Surfactants—A Review, May 2000.
Somasundaran, P., et al., Household and Personal Care Today, Silicone Emulsions—Interfacial Aspects and Applications, March 2010.
Sawynok, J., et al., Pharmacological Reviews, Topical and Peripherally Acting Analgesics, Vol. 55, No. 1, 2003.
Sullivan, W., et al., Archives Physical Medicine Rehabilitation, Industrial Medicine and Acute Musculoskeletal Rehabilitation—Medications for the Treatment of Acute Musculoskeletal Pain, Vol. 88, No. 1, March 2007.
Collins, S., et al., Pain Medicine, NMDA Receptor Antagonists for the Treatment of Neuropathic Pain, Vol. 11, No. 1726-1742, 2010.
Jorge, L., et al., Journal of Pain Research, Topical Preparations for Pain Relief—Efficacy and Patient Adherence. Vol. 4, No. 11-24, 2011.
Peralta, A., et al., RxTriad, Compounding for Pain Management and Palliative Care, Vol. 6, No. 10, Summer 2003.
Brown, S., et al., Techniques in Regional Anesthesia and Pain Management. Prescribing Flexibility through Prescription Compounding. Vol. 12, No. 119-121, 2008.
Park. C., et al., Korea-Australia Rheology Journal, Emulsion Stability of Cosmetic Creams based on Water-in-Oil High Internal Phase Emulsions, Vol. 15, No. 3, September 2003.

What is claimed:

1. A silicone gel composition comprising:
a hydrophilic silicone copolyol, wherein the hydrophilic silicone copolyol comprises phenyl trimethicone, and wherein the phenyl trimethicone is present in a concentration of about 2.0 weight percent;
a lipophilic silicone copolyol, wherein the lipophilic silicone copolyol comprises C30-45 dimethicone, and wherein the C30-45 dimethicone is present in a concentration of about 2.50 weight percent;
a non-ionic oil-in-water (O/W) emulsifier agent, wherein the non-ionic oil-in-water (O/W) emulsifier agent comprises a blend of cetearyl alcohol and ceteareth-20, and wherein the non-ionic oil-in-water (O/W) emulsifier agent is present in a concentration of about 10.00 weight percent;
a non-ionic water-in-oil (W/O) emulsifier agent, wherein the non-ionic water-in-oil (W/O) emulsifier agent comprises a copolymer of hydroxyethyl acrylate and sodium acryloyldimethyl taurate, and wherein the non-ionic water-in-oil (W/O) emulsifier agent is present in a concentration of about 1.90 weight percent;
an inorganic hydrocolloid, wherein the inorganic hydrocolloid comprises magnesium aluminum silicate, and wherein the magnesium aluminum silicate is present in a concentration of about 1.50 weight percent;
an organic hydrocolloid, wherein the organic hydrocolloid comprises hydroxypropyl starch phosphate, and wherein the hydroxypropyl starch phosphate is present in a concentration of about 0.10 weight percent;
a biocompatible surfactant with phosphatidylcholine, wherein the biocompatible surfactant comprises lecithin, and wherein the lecithin is present in an amount of about 0.33 weight percent;
a first non-polar solvent, wherein the first non-polar solvent is light mineral oil, and wherein the light mineral oil is present in an amount of about 18 weight percent; and
a second non-polar solvent, wherein the second non-polar solvent is isopropyl palmitate, and wherein the isopropyl palmitate is present in an amount of about 0.33 weight percent.

* * * * *